United States Patent [19]

Doody

[11] Patent Number: 5,172,693
[45] Date of Patent: Dec. 22, 1992

[54] PRENATAL NON-INVASIVE DETECTION OF MECONIUM STAINED AMNIOTIC FLUID

[76] Inventor: Michael C. Doody, 4203 Towanda Trail, Knoxville, Tenn. 37919

[21] Appl. No.: 465,510

[22] Filed: Jan. 16, 1990

[51] Int. Cl.$^5$ .............................................. A61B 6/00
[52] U.S. Cl. ................................... 128/633; 128/634; 128/665
[58] Field of Search ........... 128/633, 634, 637, 662.06, 128/664, 665, 775

[56] References Cited

U.S. PATENT DOCUMENTS

| | | | |
|---|---|---|---|
| 3,477,818 | 11/1969 | Fried et al. | |
| 3,923,459 | 12/1975 | Ertingshausen et al. | |
| 4,029,085 | 6/1977 | DeWitt et al. | 128/633 |
| 4,204,839 | 5/1980 | Wu et al. | |
| 4,412,005 | 10/1983 | Wu | |
| 4,479,499 | 10/1984 | Alfano | 128/665 |
| 4,785,806 | 11/1988 | Deckelbaum | 128/866 |
| 4,856,527 | 8/1989 | Karcher et al. | 128/634 |
| 4,930,516 | 6/1990 | Alfano et al. | 128/665 |
| 4,957,114 | 9/1990 | Zeng et al. | 128/665 |

FOREIGN PATENT DOCUMENTS

| | | | |
|---|---|---|---|
| 2215658 | 10/1973 | Fed. Rep. of Germany | 128/665 |
| 2916061 | 11/1979 | Fed. Rep. of Germany | 128/665 |

OTHER PUBLICATIONS

Translation of German Publication #2916061, Inventor Yamanishi et al., "A Medical Instr. to Examine Jaundice", Nov., 1979.

*Primary Examiner*—Lee S. Cohen
*Assistant Examiner*—K. M. Pfaffle
*Attorney, Agent, or Firm*—Pitts and Brittian

[57] ABSTRACT

This invention describes a process for the diagnosis of meconium stained amniotic fluid. Meconium staining is often the result of ongoing or transient fetal distress or prolonged gestation. This process involves the non-invasive illumination of the amnion with light of a specific wavelength and detecting the fluorescence of certain biological pigments contained within the meconium. The process uses a source of light and a means of selecting the desired wavelength of light, directing the light to the target area, retrieving the fluorescence, converting the fluorescent emission to an electrical signal, amplifying the signal and analyzing the signal with a data processing unit.

23 Claims, 4 Drawing Sheets

PRENATAL NON-INVASIVE DETECTION OF MECONIUM STAINED AMNIOTIC FLUID

DESCRIPTION

1. Technical Field

This invention relates generally to the field of obstetrics and gynecology and more particularly to the noninvasive prenatal diagnosis of a meconium state pregnancy.

2. Background Art

During gestation and prior to birth, the fetus, in a normal state pregnancy is continent. During its prenatal life, mucus, bile and epithelial cells build up in the fetus's colon. This buildup is known as "meconium". Meconium contains a large amount of bilirubin and its metabolites which is derived from the breakdown of fetal blood cells. In the normal pregnancy meconium is not excreted until after parturition; however, ongoing or transient stress can cause the fetus to expel meconium into the surrounding amniotic fluid. The incidence of meconium staining often increases with gestational age. This staining results in a "Meconium state pregnancy". The presence of meconium stained fluid is indicative of a need for more intensive early labor monitoring. Infants born with meconium staining have lower overall infant assessment scores than their peers born without meconium staining. Another danger associated with meconium staining is the risk of the infant inhaling meconium into its lungs at the time of birth. This results in "Meconium Aspiration Syndrome", a very severe form of pneumonia that often kills the infant or renders it a pulmonary cripple for life. Meconium aspiration syndrome is also a significant cause of cerebral palsy. Because of the lower infant assessment scores and the risk of meconium aspiration syndrome, infants born with meconium staining have a higher mortality and morbidity rate than infants born without meconium staining.

Currently meconium staining can be diagnosed only by direct visualization of the amniotic fluid. This would usually occur at the time the placental membranes rupture; an event which may not necessarily occur at an early enough stage of labor to allow the detection of meconium staining by that method to be of any practical value. Meconium can also be detected during an amniocentesis. This is an invasive procedure wherein a needle is inserted into the amniotic sac through the abdominal wall and an aliquot of amniotic fluid is withdrawn. This procedure is most often performed in order to perform certain prenatal genetic tests or protein assays. It is not performed for the sole purpose of meconium detection, and is not performed routinely. A diagnostic process that would allow a non-invasive means of detecting meconium staining in a term pregnancy is therefore needed. It is at least one object of this invention to provide a low risk non-invasive process for the detection of meconium stained amniotic fluid that could be performed at any stage of pregnancy. However, those skilled in the art will recognize that this invention could also be useful in the diagnosis of other prenatal conditions that result in the presence of increased porphyrin breakdown products in amniotic fluid.

Heretofore, various inventions have utilized the various qualities of bilirubin in order to quantify the amount of bilirubin in a fluid or to facilitate the remote gathering of fluorometric data. Known prior art methods are described in the following U.S. Pat No. 3,477,818 issued to Fried et al; U.S. Pat. No. 3,923,459 issued to Ertingshausen et al; U.S. Pat. No. 4,204,839 issued to Wu et al; and U.S. Pat. No. 4,412,005 issued to Wu. However, in light of the need for a noninvasive in vivo procedure, the prior art has the disadvantage that it relies either on wet/dry in vitro chemistry procedures or invasive in vivo processes, i.e. catheterization.

DISCLOSURE OF THE INVENTION

This invention is the first to consider the non-invasive in vivo detection of meconium in amniotic fluid. The invention is non-invasive in that the light is passed transcutaneously, transabdominally, transvaginally, transcervically or transamniotically. Due to the fact that different skin colors absorb light with different degrees of efficiency, the preferred embodiment would be transvaginally.

Because human tissue is capable of passing the excitation as well as the emission wavelengths characteristic of the fluorescent pigments contained in meconium with a minimum of attenuation, the excitation wavelength of bilirubin and other biological pigments can be passed through tissue and into the amniotic fluid. This light is absorbed by the fluorescent pigments of meconium, if present, and emitted at a slightly longer wavelength. This emission fluorescence can be filtered and focused into a receiving device, amplified and then displayed or analyzed. A positive readout would be indicative of the presence of meconium.

The means wherein this process would be accomplished would consist of an excitation light source and a detector. The excitation side would consist of a light source, a transmission device, a means of spectral isolation of the appropriate wavelengths for the excitation of the fluorescent pigment in question and a transparent patient-probe interface.

The above-mentioned detector would consist of a means of spectral isolation that would only allow light in the range of the emission band to pass through and would detect any fluorescence being emitted by the bilirubin pigments in the meconium. The emission side of the probe could also contain a second detector; The second detector would determine how much light is being scattered and reflected by the tissue. The detectors would consist of a means of isolating the appropriate wavelength of light, a photosensor, a means of transmitting a signal away from the sensor, an amplifier coupled with data processing circuitry and a readout device.

BEST MOST FOR CARRYING OUT THE INVENTION

Figure 1:
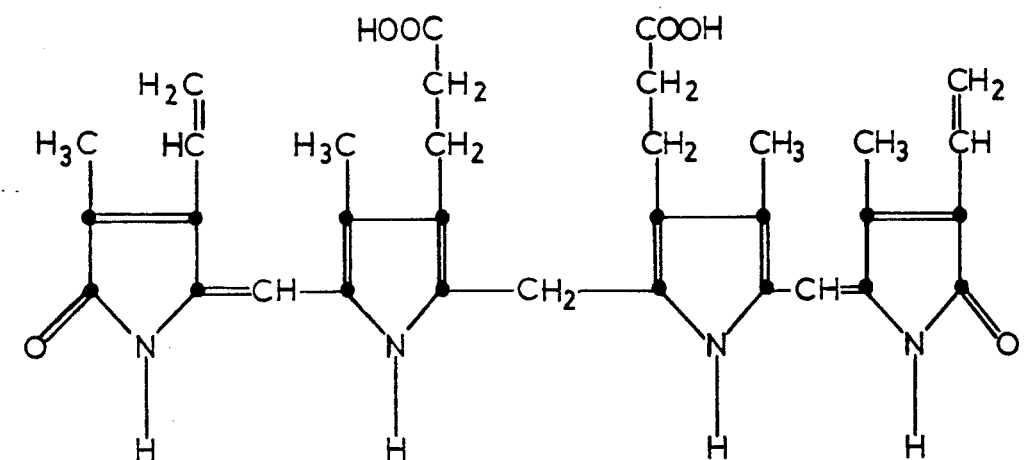
FIG. 1 shows the molecular structure of unconjugated bilirubin. The unconjugated form is the most prevalent form.

Bilirubin is a nitrogen containing organic compound (see FIG. 1) that is weakly fluorescent, i.e. it absorbs light of a particular wavelength and emits it at a slightly longer wavelength.

Figure 2:
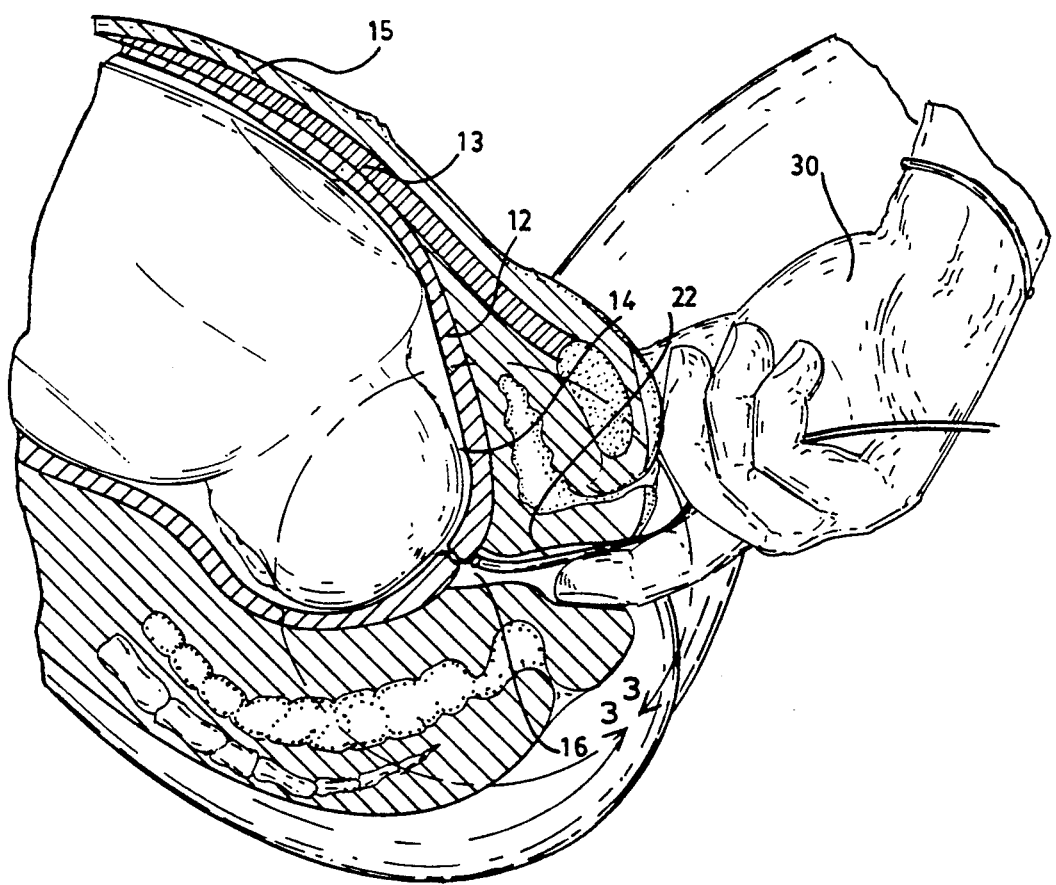
FIG. 2 shows the relative position of the gravid female and the fetus after lightening and during one possible method of examination.
Figure 3:
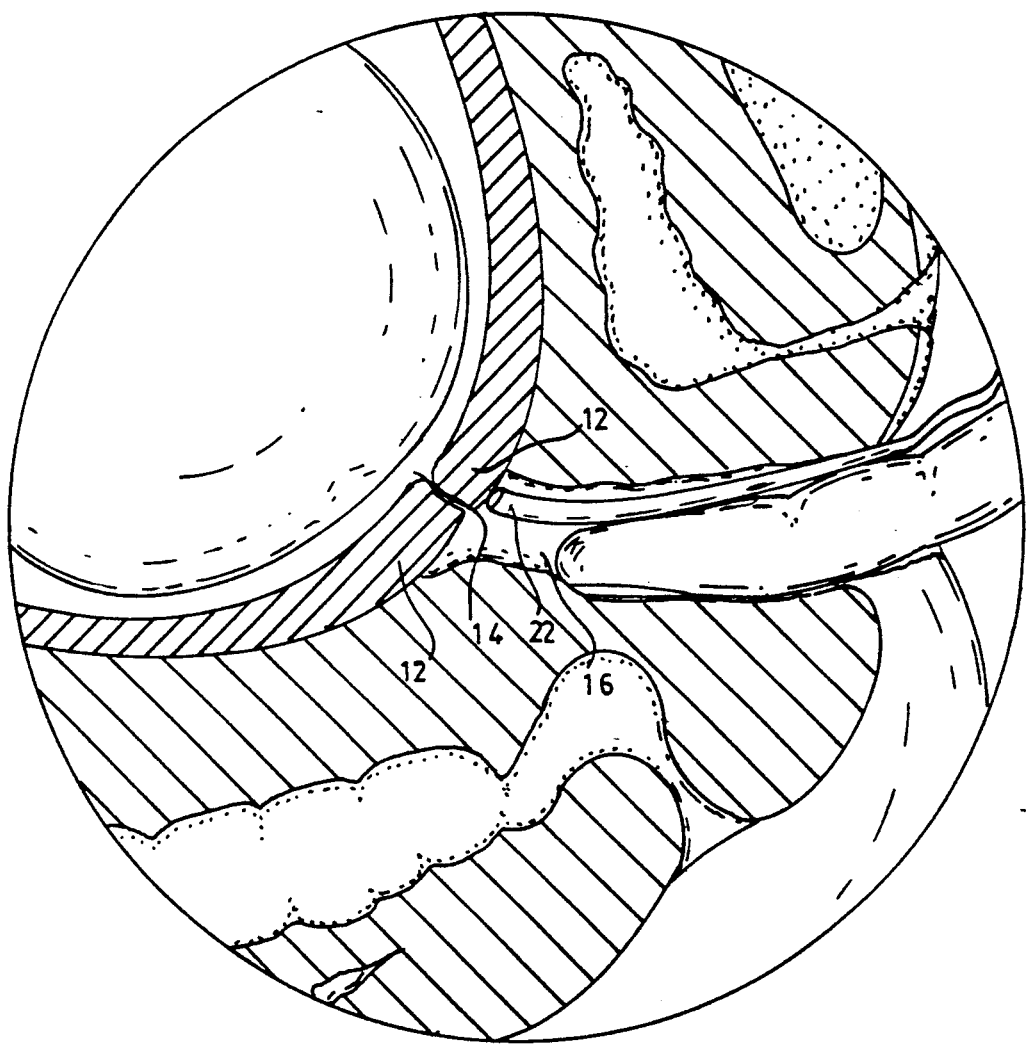
FIG. 3 is an enlarged fragmented view of the encircled area in FIG. 2 designated at 3—3. It shows the placement of the probe in the preferred embodiment of the invention.

The present invention could detect meconium either transcutaneously, transabdominally, or transvaginally. The preferred embodiment would be transvaginally due to the effects different skin colors have on the efficiency with which skin absorbs light and the fact that the transvaginal route of detection reduces the amount of tissue that the light must pass through. A typical arrangement is illustrated at FIGS. 2 and 3. The examining physician's hand 30 introduces the probe 22 into the vagina 16 and places the probe 22 against the uterine wall 12. Light from the probe 22 is then passed through the uterine wall 12 and into the amniotic cavity 14 which is filled with amniotic fluid. As can be seen, by passing the light directly across the uterine wall 12, by directing the probe 22 through the vagina 16, the light does not have to pass through the abdominal muscles 13 and fatty tissues 15 thereby significantly reducing the amount of light attenuation due to tissue interference.

Figure 6:
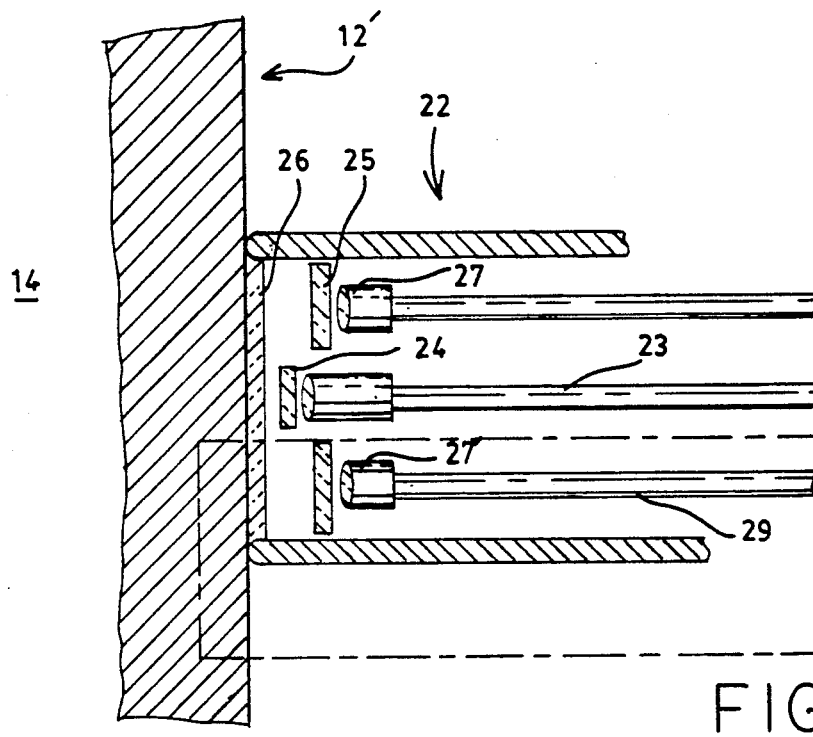
FIG. 6 is a representation of one possible configuration of the probe and uterine wall utilized by the invention.

As illustrated at FIG. 6, a fiber optic 23 is used to carry the light beam which is passed through a spectral isolation means 24, which will be recognized by those skilled in the art to include filters, prisms, gratings and monochromatic lasers, used to spectrally isolate the excitation wavelengths; the light then passes through the transparent patient-probe interface 26 and across the tissue layer 12'. The thickness of the layer will vary depending upon which route of transmission the user chooses, i.e. transabdominal or transvaginal. The fluorescence that is emitted by the bilirubin passes through the tissue layer and into the probe where it is detected by photosensors 27 and 27.

As the light leaves fiberoptic 23, some of it will be reflected by the various layers. Most of this reflected light will be blocked by the further spectral isolation means 25, which will be recognized by those skilled in the art to include filters, prisms and gratings, used to isolate the emission wavelength. It is possible that some of this light will leak through the further spectral insulation means. The second detector shown as 29 will detect this reflected light and its wavelength will be electronically "subtracted" out of the amplified and analyzed signal so that the displayed signal is the spectra of the fluorescence.

Figure 7:
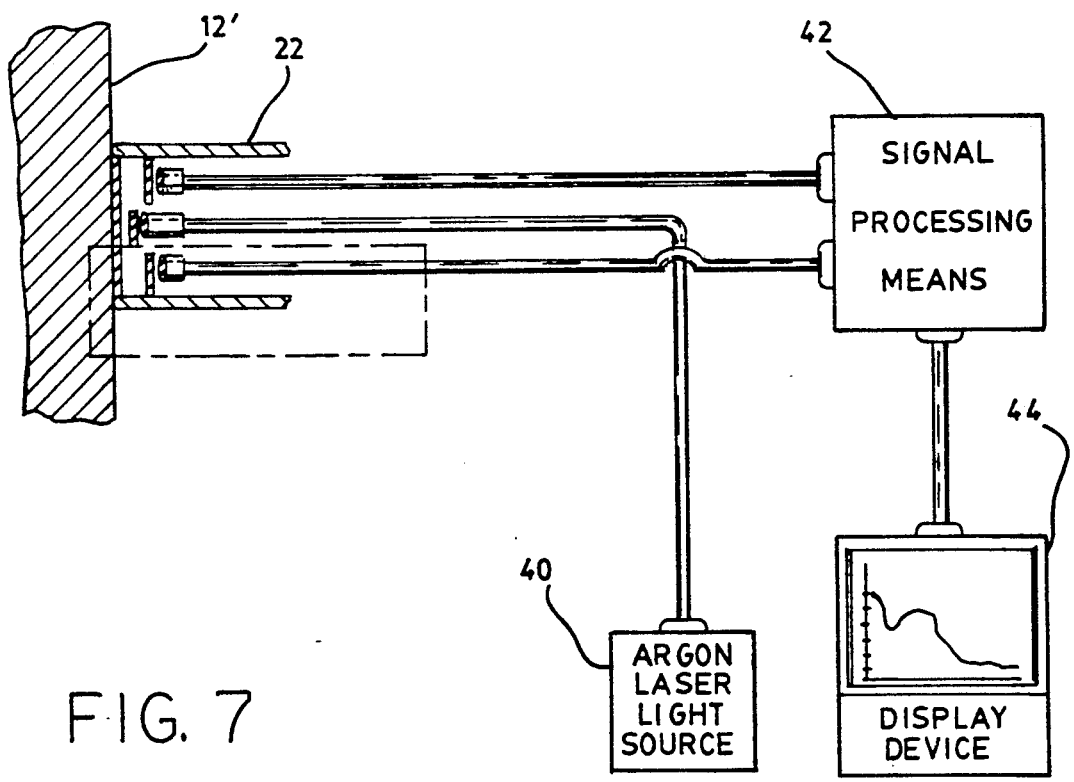
FIG. 7 shows a diagrammatic view of the system utilized by the present invention.

As illustrated at FIG. 7, the signal generated by the detector(s) within probe 22 is then processed by the signal processing means 42. The output generated by said processing means is then displayed by the display device 44. The light source 40 could be incandescent, fluorescent, arc lamp, laser or any other suitable artificial light source. The beam could be continuous, interrupted, modulated or otherwise variable. The preferred embodiment of this invention would utilize an argon laser. The tissue that the light will be traveling through contains large amounts of hemoglobin. Hemoglobin absorbs light very efficiently. An argon laser emits light in the very narrow excitation range which is very close to the minimum absorption curve of hemoglobin's spectra. By use of an argon laser a minimum of light will be lost to hemoglobin absorption.

Figure 4:
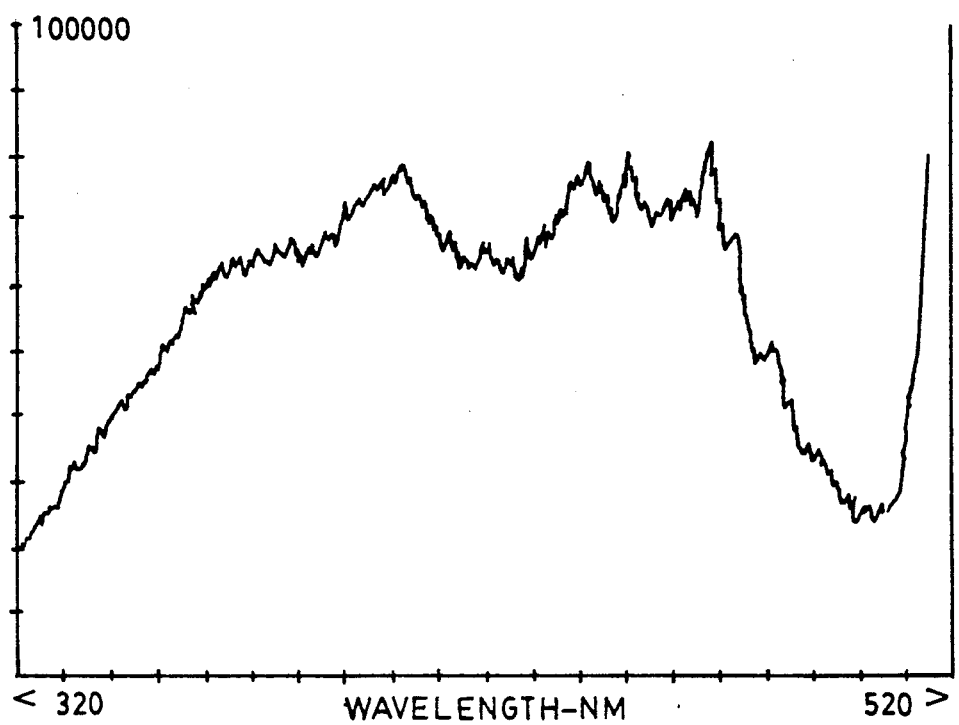
FIG. 4 shows the excitation spectra of meconium stained amniotic fluid (1:30 dil.) when the wavelength of emission is 515 nm.
Figure 5:
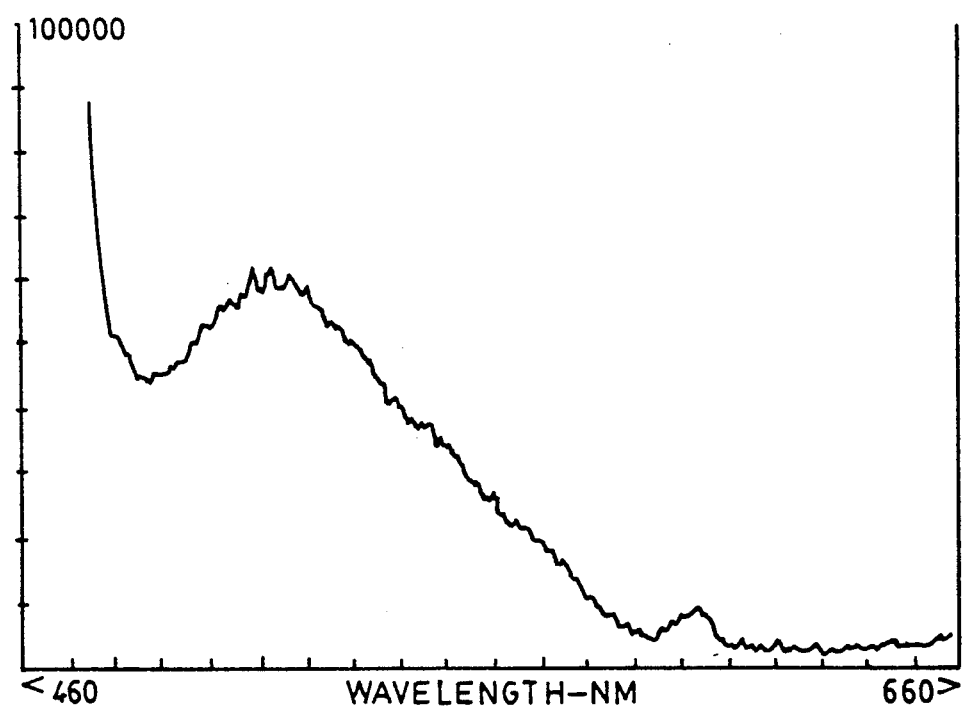
FIG. 5 shows the emission spectra of meconium stained amniotic fluid (1:30 dil.) when the wavelength of excitation is 465 nm.

The excitation wave length of the bilirubin metabolites and other biological pigments in meconium is in the range of 300 nm to 525 nm. (see FIG. 4). The method of isolating this band of light is best accomplished with an interference filter selected for this range when monochromatic laser light is not used. Other acceptable means would include, but not be limited to, equivalent bandpass filters, prisms, or gratings. The emission wave length of the pigments in meconium is 460 nm to 610 nm as illustrated at FIG. 5. The method of isolating this band of light is best accomplished with an interference filter selected for this wavelength. Other acceptable means would include, but not be limited to, equivalent bandpass filters, prisms, or gratings.

Due to the fact that there may be some leakage of reflected excitation light through the emission detector filter, a second detector, as illustrated at FIG. 6, may be utilized to determine the amount of reflected excitation light. This information will allow the formulation of an index that will allow a determination that the light being received, amplified and displayed is actually emitted fluorescence.

The drawings and descriptions herein are only intended to describe one possible means of practicing this invention. They are not intended in any way to limit this invention. Those skilled in the art will readily recognize the utility of this invention in diagnosing other prenatal conditions that result in the buildup of porphyrin breakdown products within the amniotic fluid.

I claim:

1. A process for a non-invasive in vivo detection of a meconium state pregnancy in a gravid female by detection of fluorescent pigments within meconium stained amniotic fluid, said process comprising steps:
    A. spectrally isolating excitation wavelengths characteristic of said pigments;
    B. passing said isolated excitation wavelengths into said amniotic fluid for exciting said fluorescent pigments contained within said meconium;
    C. detecting fluorescence emitted by said excited pigments contained within said meconium;
    D. spectrally isolating emission wavelengths characteristic of the fluorescence emitted by said pigments contained in the meconium and
    E. amplifying and analyzing spectra of said detected fluorescence.

2. The process of claim 1 wherein said excitation wavelengths are passed into said amniotic fluid transcutaneously.

3. The process of claim 1 wherein said excitation wavelengths are passed into said amniotic fluid transabdominally.

4. The process of claim 1 wherein said excitation wavelengths are passed into said amniotic fluid transvaginally.

5. The process of claim 1 wherein said excitation wavelengths are passed into said amniotic fluid transcervically.

6. The process of claim 1 wherein said excitation wavelengths are passed into said amniotic fluid transamniotically.

7. The process of claim 1 wherein said excitation wavelength is in a range of about 300 to about 525 nm.

8. The process of claim 1 wherein said excitation wavelength is spectrally isolated by means of a monochromatic laser.

9. The process of claim 1 wherein said emission wavelength is in a range of about 460 to about 610 nm.

10. A process for a non-invasive in vivo detection of a meconium state pregnancy in a gravid female by detection of bilirubin and its metabolites within meconium stained amniotic fluid, said process comprising steps:

A. spectrally isolating excitation wavelengths characteristic of said bilirubin in a range of about 300 to about 525 nm by means of a monochromatic argon laser;

B. passing said isolated excitation wavelengths transcervically into said amniotic fluid for exciting fluorescent pigments contained within said bilirubin by said meconium;

C. detecting fluorescence emitted by said excited pigments contained within said meconium;

spectrally isolating emission wavelengths in a range of about 460 to about 610 nm characteristic of said fluorescence emitted by said bilirubin contained in said meconium by means of a filter and E. amplifying and analyzing spectra of said detected fluorescence.

11. The process of claim 10 wherein said excitation wavelengths are passed into said amniotic fluid transcutaneously.

12. The process of claim 10 wherein said excitation wavelengths are passed into said amniotic fluid transabdominally.

13. The process of claim 10 wherein said excitation wavelengths are passed into said amniotic fluid transvaginally.

14. The process of claim 10 wherein said excitation wavelengths are passed into said amniotic fluid transamniotically.

15. A process utilizing fluorescent spectroscopy for non-invasively detecting a prenatal meconium state pregnancy in the gravid female by in vivo detection of fluorescent pigments in amniotic fluid wherein said pigments are bilirubin and its metabolites, said process comprising steps:

A. illuminating amniotic fluid with monochromatic light at a wavelength required for excitation of said fluorescent pigments contained within meconium thereby causing said pigments to fluoresce and emit photons;

B. detecting said emitted photons emitted by said excited pigments contained within said meconium thereby generating a signal representative of said emitted photons; and C. amplifying and analyzing said generated signal.

16. The process of claim 15 wherein said light is passed into said amniotic fluid transcutaneously.

17. The process of claim 15 wherein said light is passed into said amniotic fluid transabdominally.

18. The process of claim 15 wherein said light is passed into said amniotic fluid transvaginally.

19. The process of claim 15 wherein said light is passed into said amniotic fluid transcervically.

20. The process of claim 15 wherein said light is passed into said amniotic fluid transamniotically.

21. The process of claim 15 wherein said wavelength required for excitation of said fluorescent pigments is in a range of about 300 to about 525 nm.

22. The process of claim 15 wherein said emitted photons has a wavelength in a range of about 460 to about 620 nm characteristic of fluorescence emitted by said bilirubin.

23. The process of claim 15 wherein said monochromatic light is an argon laser.

* * * * *